United States Patent [19]

Mattson et al.

[11] Patent Number: 4,672,648

[45] Date of Patent: Jun. 9, 1987

[54] APPARATUS AND METHOD FOR RADIATION ATTENUATION

[75] Inventors: Rodney A. Mattson, Mentor; Gordon D. DeMeester, Wickliffe, both of Ohio

[73] Assignee: Picker International, Inc., Highland Hts., Ohio

[21] Appl. No.: 791,210

[22] Filed: Oct. 25, 1985

[51] Int. Cl.[4] .................. H01J 35/16; G21K 1/02
[52] U.S. Cl. ........................ 378/4; 378/149; 378/158
[58] Field of Search .......... 378/4, 7, 149, 158, 378/154, 147

[56] References Cited

U.S. PATENT DOCUMENTS

| | | | |
|---|---|---|---|
| 1,164,987 | 12/1915 | Bucky | 378/154 |
| 2,216,326 | 10/1940 | Smith | 378/158 |
| 2,638,554 | 5/1953 | Bartow et al. | 378/147 |
| 3,755,672 | 8/1973 | Edholm et al. | 378/158 |
| 3,829,701 | 8/1974 | Hura | 378/153 |
| 3,921,000 | 11/1975 | Muehllehner | 378/149 |
| 3,937,963 | 2/1976 | Hounsfield | 378/18 |
| 4,052,620 | 10/1977 | Brunett | 364/414 |
| 4,096,391 | 6/1978 | Barnes | 378/146 |
| 4,101,768 | 7/1978 | Lill | 378/7 |
| 4,255,664 | 3/1981 | Rutt | 378/5 |
| 4,277,684 | 7/1981 | Carson | 378/7 |
| 4,286,167 | 8/1981 | La Riviere | 378/158 |
| 4,304,999 | 12/1981 | Richey et al. | 378/4 |
| 4,347,440 | 8/1982 | Haas | 378/156 |

FOREIGN PATENT DOCUMENTS

| | | | |
|---|---|---|---|
| 528479 | 12/1927 | Fed. Rep. of Germany | 378/149 |
| 2619008 | 11/1977 | Fed. Rep. of Germany | 378/147 |

*Primary Examiner*—Carolyn E. Fields
*Assistant Examiner*—Constantine Hannaher
*Attorney, Agent, or Firm*—Timothy B. Gurin

[57] ABSTRACT

An off-focal radiation collimator is disclosed which includes a plurality of radiation absorbing elements supported in spaced relationship with respect to one another in a housing such that each element is aligned along radii extending from the focal spot of a radiation source. The off-focal collimator is preferably disposed between the radiation source and a primary beam collimator. The off-focal collimator also acts as a radiation beam compensator. By varying the spatial density of the radiation absorbing elements by a function of location within the housing, the radiation beam can be shaped to any desired profile.

24 Claims, 10 Drawing Figures

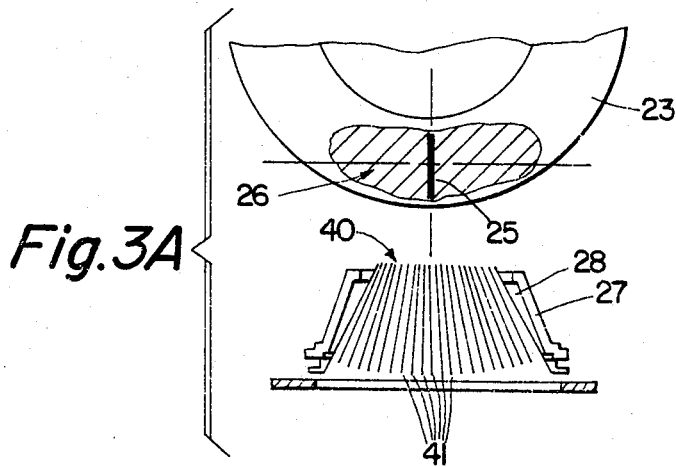
Fig.3A
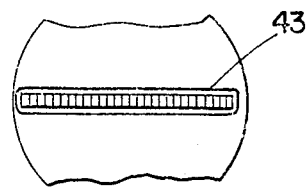
Fig.3B
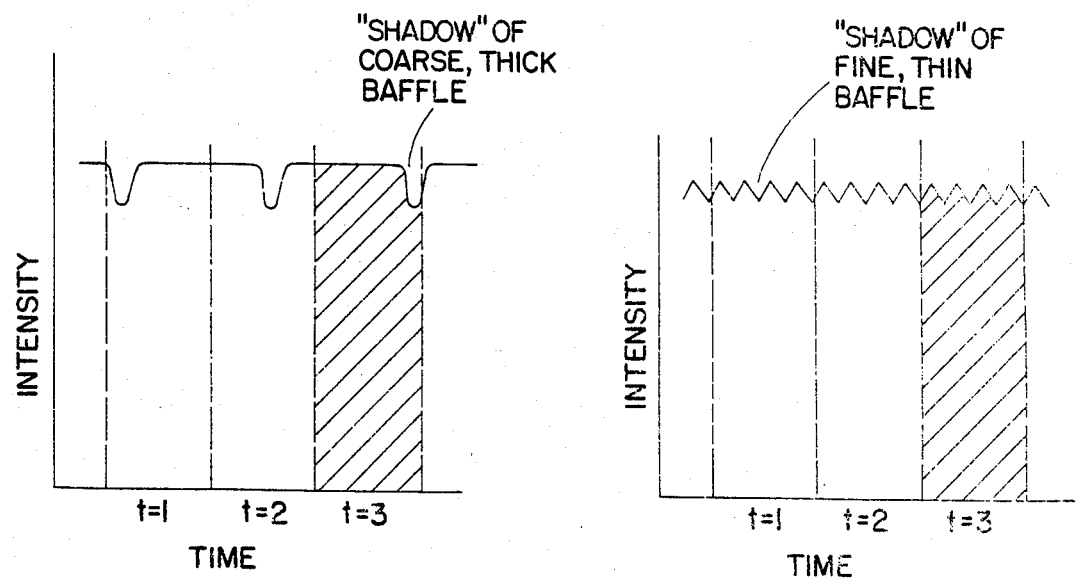
Fig.4A
Fig.4B

VARIABLE BAFFLE SPACING CONSTANT THICKNESS

VARIABLE THICKNESS CONSTANT SPACING

APPARATUS AND METHOD FOR RADIATION ATTENUATION

DESCRIPTION

TECHNICAL FIELD

The present invention relates generally to the field of radiation imaging and, more particularly, to computed tomography X-ray scanners. The invention deals with a method and apparatus for improved attenuation of off-focal radiation and beam compensation. It is to be appreciated, however, that the invention may find further application in other medical diagnostic equipment such as medical diagnostic digital radiography.

BACKGROUND ART

In computed tomography a two-dimensional image of a subject under examination is generated from multiple one-dimensional projections. A source of X-radiation transmits a beam of radiation through plural co-planar paths defining a cross-section of the subject under examination. The intensity of the attenuated radiation passing through the subject is monitored by one or more detectors whose electrical output is indicative of the radiation intensity impinging on the detector. The detectors are often single scintillation crystals, each optically coupled to a different photodiode.

So-called fourth generation CT scanners include a stationary array of detectors and a moving X-ray source. The detector array typically surrounds a patient aperture or scan circle which defines a patient scanning plane. The X-ray source when energized radiates the plane from a number of different directions as it orbits about the scan circle and the detectors measure the X-ray intensity of attenuated radiation passing through the patient.

The current fourth generation CT scanner designated as the Synerview 1200 is commercially available from Picker International, Inc. of Highland Heights, Ohio.

The radiation source typically employed in fourth generation CT scanners produces a diverging cone of radiation. A mechanical collimator is generally employed in conjunction with the source to limit the divergence of the cone to a fan-shaped swath which is confined to the patient scanning plane and to an angle which encompasses the subject under examination.

The X-ray beam is emitted from a small area on an X-ray tube anode known as the focal spot. A cathode assembly emits and directs electrons toward the anode. The trajectories of electrons are shaped into a beam of closely controlled dimensions. When a high voltage potential is applied to the X-ray tube, the electrons strike the anode in an approximately rectangular pattern. As a practical matter, however, X-radiation is produced at other locations other than the focal spot. Off-focal radiation is usually generated by secondary electrons that have been reemitted from the focal spot and return to the anode at points remote to the focal spot and produce X-rays at their point of impact. As many as 50% of the primary electrons are backscattered of which roughly one-half have an energy close to the primary beam and thus capable of producing off-focal radiation. In CT scanning systems, three to eight percent of the radiation detected has originated at points other than the focal spot.

The result is a broad low level X-ray source which projects its radiation to all points that are unshielded or uncollimated thence through any object to be radiographed. Small objects or sharp edges lose any proper definition because of the diffuse source. The lack of definition gives rise to non-linear artifacts in the reconstructed image. The mechanical collimator described above is able to occlude some but not substantially all of the off-focal radiation. The mechanical collimator is least effective in attenuating off-focal radiation in the central portion of the emergent beam.

In the above-described CT scanning systems, it has been found desirable to shape the intensity distribution of the X-ray beam across its angular extent. Shaped attenuation filters or compensators are currently employed and typically consist of wedges or contoured sections of plastic, aluminum, copper or composites of various material. These devices shape the radiation intensity of the beam to better match the attenuation characteristics of the subject under examination by absorbing radiation in a spatially controlled manner. By shaping the beam intensity in this fashion, the total dose to the subject under examination is reduced. The overall system radiation level can be increased to achieve a decrease in system noise since the range of radiation intensity emanating from the object under examination is reduced so as not to exceed the dynamic range of the detectors. These devices bear names such as dodgers, dose compensators and bow-tie filters.

A disadvantage of interposing such an element in the X-ray beam is X-ray spectrum modification by photoelectric absorption or beam hardening. Another disadvantage is the production of unwanted scatter radiation by the coherent and incoherent interactions of the filter with the X-ray beam. These secondary effects may influence the fidelity of the image reconstruction process, hence the quantitative accuracy of the CT scanner.

An additional phenomenon occurs due to the broad low-level radiation source (off-focal radiation). Small objects under examination are particularly susceptible to an unusual artifact which occurs due to interactions with an X-ray beam compensator and the off-focal radiation. For example, the image of a small cylindrical object, centrally located in the scan circle, changes from a circle with a circular central artifact to a crescent-shaped artifact, as the object is moved to the periphery of the scan circle. This phenomenon makes it very difficult to derive any quantitative information from the CT number of the image of the scan of such an object. The quantitative accuracy of the CT numbers that represent the image is degraded since the X-ray paths whose intensity is measured by the detector do not all emanate from a single point. Due to the off-focal radiation, the ray paths to the detector cut a broader path through the object than that accounted for by the reconstruction algorithms, and hence are less faithfully reconstructed.

Alterations in the reconstruction algorithm of compensate for these difficulties is complicated by the fact that the projection of the off-focal radiation varies depending on the position of a detector in the X-ray fan beam and whether a dose compensator is present. For example, off-focal radiation from the left most side of the anode is occluded by the left most edge of the primary collimator. However, the primary collimator does not occlude any off-focal radiation for a centrally located detector. Similarly the ray paths through a compensator are unequally attenuated through different portions of the X-ray fan. Any mathematical characterization of this phenomenon is complicated.

It is an object of this invention to provide a radiation attenuator which substantially eliminates off-focal radiation emanating from the radiation source and which compensates the beam profile without substantially changing the energy spectrum of the beam or creating substantial quantities of scatter radiation.

SUMMARY OF THE INVENTION

The disadvantages of the prior art as described above are reduced or eliminated by the provision of an improved radiation attenuator. A secondary collimator, interposed between the radiation source and a primary collimator, includes a plurality of radiation absorbing plates supported in spaced relationship with respect to one another in a housing such that each plate is aligned along radii extending from the focal spot of the radiation source.

The attenuator as described thus provides a means wherein off-focal radiation originating from points other than the focal spot of the radiation source is substantially blocked. The attenuator has particular utility in blocking off-focal radiation occurring in the central portion of the emergent beam.

In accordance with another aspect of the present invention, the attenuator as described acts as a radiation dose compensator. The array of radiation absorbing elements are mounted such that the spatial density of the elements varies as a function of dose compensation desired. The attenuator thereby provides dose compensation to the object being examined without causing appreciable spectral changes to the radiation beam and without creating appreciable scatter radiation.

Varying the spatial density of the elements of the attenuator to compensate the dose received by the object under examination can be achieved in many ways. To illustrate, a specific embodiment of the invention will be considered. In such an embodiment, the center-to-center spacing of the elements is held constant and the thickness of the elements varies as a function of their location within the attenuator housing.

In another embodiment, the thickness of the elements is held constant and the center-to-center spacing of the elements varies as a function of their location within the attenuator housing.

In either of the two embodiments, the spatial density of the elements preferably increases with the distance from the center of the housing. In this fashion, the intensity of radiation beam is reduced at the outer extents while the intensity remains substantially unattenuated in the central portion of the beam profile.

These and other aspects and features of the present invention will become apparent upon reading and understanding the following detailed description of the preferred embodiment.

BRIEF DESCRIPTION OF THE DRAWINGS

The invention may take form in various steps and arrangements of steps or in various components and arrangements of components. The drawings are only for purposes of illustrating a preferred embodiment and are not to be construed as limiting it.

FIGS. 3A and 3B, respectively, are front and bottom diagrammatic illustrations of the secondary collimator in accordance with the present invention;

FIGS. 4A and 4B are graphical representations of the benefit to using thin baffles in accordance with the present invention;

BEST MODE FOR CARRYING OUT THE INVENTION

Figure 1:
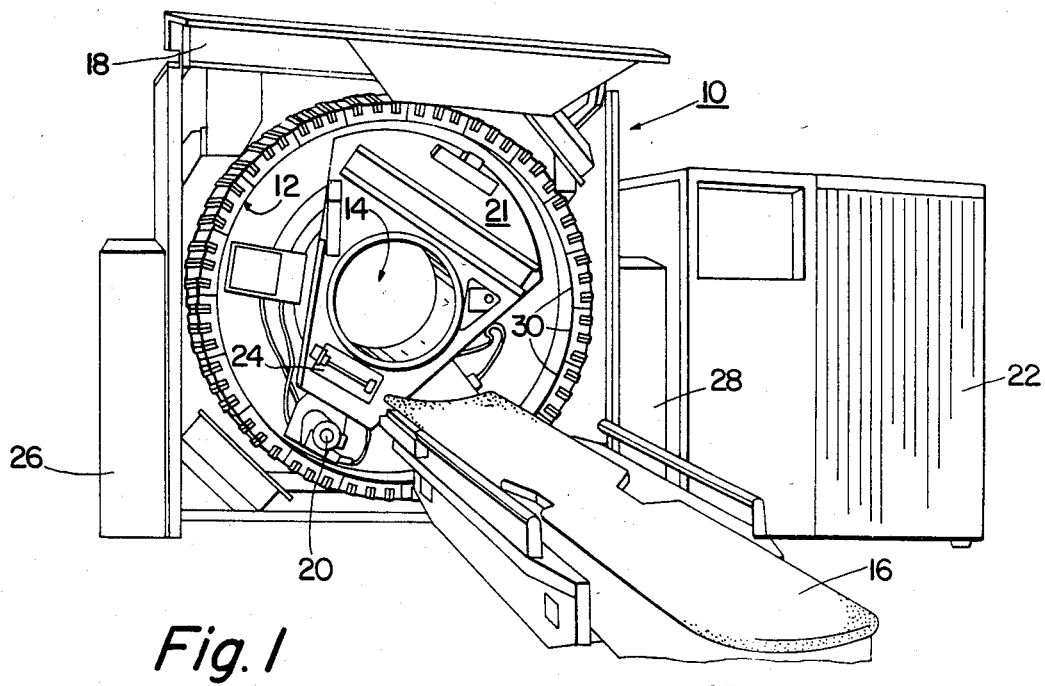
FIG. 1 is a diagrammatic illustration of a computed tomography scanner in accordance with the present invention.

Turning now to the drawings, FIG. 1 illustrates a computed tomography scanner 10 used in imaging cross-sectional slices of interest in a patient. While the invention can be employed in any CT geometry, the scanner as shown at 10 is a fourth generation computed tomography scanner where a fixed array 12 of detectors surrounds structure defining a scan circle or patient aperture 14. During imaging, a patient is positioned on a couch 16 and then moved into and through the patient aperture 14 until a cross-sectional slice to be imaged is appropriately positioned. A scanner front panel 18 is hinged to the scanner housing. Two panel portions swing away from their closed position to allow the interior of the scanner 10 to be accessed. The scanner housing is supported by a pair of supports 26, 28 and can be tilted about an axis extending through the supports parallel to the floor. In this way, patient cross-sections other than a vertical cross-section can be obtained without repositioning the patient.

The generation and detection of X-radiation requires a series of electronic subsystems. These electronic subsystems produce high voltage to energize the X-ray source, analyze intensity values from the scanner detectors as well as control movement of an X-ray tube while coordinating this movement with the analysis of the output signals.

High speed computed tomography scanning is possible only through use of a high speed data processing computer system 22. The computer system 22 performs the data processing for reconstructing a grid-like mapping of density variations inside the patient slice from intensity readings taken from the detector array surrounding the patient aperture. The computer system is responsible for analyzing and reconstructing cross-sectional image densities and for displaying this information on a console (not shown).

During scanning, the X-ray tube 20 generates an X-ray beam which is shaped by a primary collimator 24 to provide a generally planar fan-shaped swath of radiation that passes through the scan circle 14 to opposed detectors in the array 12. The X-radiation is attenuated by the patient (or any other objects in the path of the X-radiation) and its intensity is then detected by detectors in the array 12. The tube 20 and the primary collimator 24 are both mounted to a gantry 21 which is rotatably mounted to the scanner 10. A motor (not shown) imparts rotational motion to the gantry 21 which is journalled on stationary portions of the scanner 12 by a bearing (not shown) which surrounds the patient aperture.

The array 12 of detectors is made up of individual modules 30 which each support a plurality of closely spaced detectors in fixed relation around the patient aperture 14. In accordance with a preferred design, each module 30 supports sixty detectors so that the twenty modules comprising the array 12 supports 1200 detectors in a circular array.

Each detector comprises a scintillation crystal coupled to a photodiode which, in turn, is mounted to a ceramic mounting block. The detector is encapsulated in an aluminum can which reflects visible light while allowing X-radiation to be freely transmitted to the scintillation crystal. In operation, the X-radiation from the X-ray tube impinges upon the scintillation crystal which converts the X-radiation to visible light which, in turn, affects the current flow in the photodiode. Changes in current produced by the X-radiation are converted from an analog current signal into a sequence of pulses which are counted.

Electronics for generating these pulses in response to current changes in the photodiode are known in the art. The pulses are then counted and divided by the time period in which they are counted to obtain an indication of the intensity of the X-radiation impinging upon the detector at a given time. Circuitry for performing this counting function is disclosed in U.S. Pat. No. 4,052,620 issued to Brunnett and owned by the assignee of the present invention and which is hereby expressly incorporated by reference.

Figure 2A:
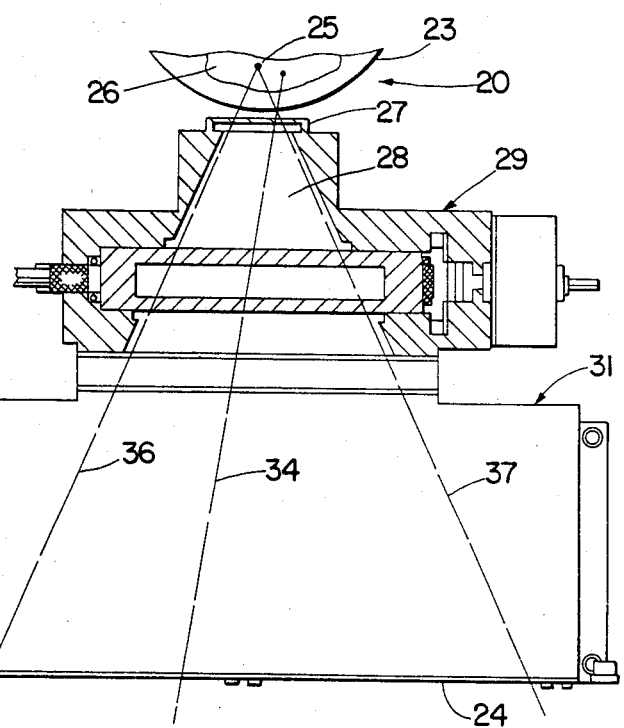
FIGS. 2A and 2B are frontal and bottom views, respectively, of the X-ray tube assembly and primary collimator assembly.
Figure 2B:
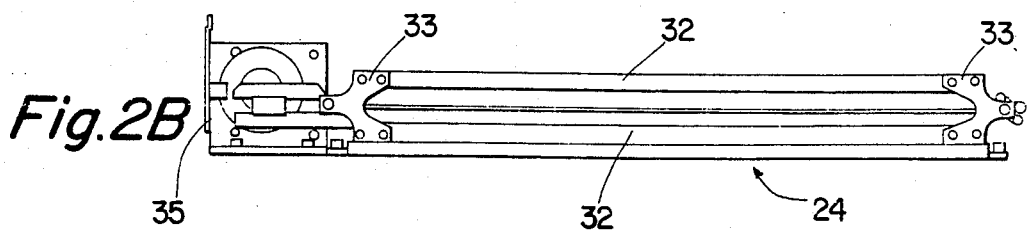

Turning now to FIGS. 2A and 2B, detail of the X-ray tube assembly and primary collimator are shown. The X-ray tube 20 consists of a cathode (not shown) which directs electrons towards a rotating anode 23. The electrons are accelerated in the direction of the anode by virtue of a high potential difference, e.g., 150 kVp between the anode and cathode. The cathode acts to focus the stream of electrons to a point on the anode known as the focal spot 25. The anode is typically made of tungsten or similar metal with a high melting point. The deceleration of the electrons as they strike the anode produces poly-chromatic radiation. The radiation produced is multi-directional, but generally propagates towards a port 27 due to the inclined face of the anode. The port 27 is part of an X-ray tube housing (not shown).

The X-ray beam passes through several components (described in more detail below) which shape the beam geometry as well as the intensity profile.

After passing through the beam port, the X-ray beam passes through an area designated at 28, through a shutter assembly 29, through a beam compensation assembly 31 and through the primary collimator assembly 24.

The shutter assembly 29 prevents the passage of X-rays until an appropriate signal is received. Once the desired rotational velocity of the gantry 21 is achieved, the computer system 22 generates a signal which commands the shutter assembly to open thus allowing the passage of the X-ray beam.

The beam compensation assembly 31 houses components which make up conventional beam compensators or filters, described above, which are selectively interposed in the beam path to shape the intensity distribution of the emergent beam.

Since the shutter and beam compensation assemblies are of known construction, they are only briefly described.

The primary collimator assembly 24 consists of two radiation absorbing vanes 32 which lay on a common plane in the path of the X-ray beam. The vanes 32 are movable with respect to one another so that the desired thickness of the beam can be varied. End plates 33 define part of a structure for imparting motion to the vanes 32. End plates 33, also made of radiation absorbing material, are used to define the overall width of the resultant beam. Motor assembly 35 drives the vanes 32 to a desired position via a command signal from the operator console (not shown).

It can be seen from the above description and drawings that radiation propagating from focal spot 25 emanates from the primary collimator 24 as a fan-shaped swath of radiation with a finite thickness. This construction, without more, also allows radiation that is produced from an area 26 around the focal spot 25 to pass into the patient aperture 14. For example, an off-focal ray 34 may pass as well as on-focal rays such as 36, 37. The manner and structure by which the off-focal radiation is eliminated is described below.

Referring to FIGS. 3A and 3B, apparatus comprising the present invention is shown in more detail. FIG. 3A depicts the relative positions of the secondary collimator 40, X-ray tube anode 23, focal spot 25 and the region of origin 26 of off-focal radiation.

The secondary collimator assembly 40 is disposed in the beam port 27 in area 28 which lies between the focal spot 25 and the primary collimator 24. Placement in this area ensures that the secondary collimator is positioned, and thus off-focal radiation is attenuated, prior to the object under examination. Placement in the beam port 27 also ensures that the secondary collimator 40 is placed as close as possible to the focal spot 25. The need for placement of the secondary collimator in close proximity to the X-ray source will be discussed in more detail below.

The secondary collimator 40 is comprised of a plurality of thin, highly absorbing elements or baffles 41 mounted in a housing 43. The housing is shaped to fit into the beam port 27. The baffles 41 are mounted within the housing in spaced relationship to one another such that their respective longitudinal dimension is aligned with radii extending from the center of the focal spot 25. FIGS. 3A and 3B show the baffles aligned in a uniformly spaced relationship. However, as will be described below, non-uniform spacing is used when beam compensation as well as attenuation of off-focal radiation is desired.

The baffles can be made of tungsten, tantalum, molybdenum or other material that is highly absorbent of X-radiation.

By placing the secondary collimator 40 into the beam path, a certain amount of useful on-focal radiation will be absorbed as well. An example of a minimum configuration of such a collimator contains 0.05 mm thick sheets of material 30 mm long and 5 mm high at 2° intervals over the angular extent of the X-ray fan beam. The width of the collimator must be adequate to cover the width of the fan beam. The height of the secondary collimator should exceed the thickness of the fan beam.

It is desirable to use thin, short baffles to reduce the effects of any focal spot beam walk or target wobble. Finer divisions of the collimation of the fan beam reduces the temporal effects of the movement of the X-ray focal spot and simplifies any corrections of those effects. The following description illustrates this principle.

A calibration scan (without subject in beam path) is made. $I_o(n,t)$ defines the unattenuated intensity of X-rays at each detector for each sampling interval where n is the detector number and t is the sample interval number. Second measurements, I(n,t) are taken with the subject being examined in the beam path. The ratios, I(n,t)/ I (n, t) are computed for values of n=0, 1199 and t=1, 1024.

In principle, perfect registration of all elements in the beam path is required. In practice however, small, slowly varying misregistrations between the calibration and examination scans occur and are permissible. Small errors in the relative position of radiation emanating from the focal spot that effects the measurement I(n,t) occur. Movement of the focal spot due to mechanical deflections, themal effects within the X-ray tube, target wobble and measurement timing "jitter" may cause misregistration errors.

Referring to FIGS. 4A and 4B the effect of the introduction of an off-focal collimator in accordance with the present invention is explored. FIG. 4A shows the response of an arbitrary detector, n, as a function of time (sample interval) with an array of coarse, long baffles interposed in the beam path. For example, it is seen that small movement in the interval, t=3, would cause relatively large changes in the area under the curve, I(n,3) due to the course "shadow" cast upon the detector by the off-focal collimator baffle. FIG. 4B is the response of the same detector to movements of an array of finely spaced, thin, short baffles interposed in the beam path. The integral of the detected current is seen to be less susceptible to small changes in apparent position of projections of shadows cast by the baffles on the detectors. It is therefore preferable to use a dense array of short thin baffles to minimize errors in the measurement of X-ray intensity. However, as explained above, the thicker baffles aggravates the effect caused by data collection registration errors. Therefore, the number of baffles or plates and their thickness is a compromise between the sacrifice of useful "on-focal" radiation, practical assembly methods, baffle material, available space in the beam port 27 and perturbations to conventional scanner operation.

Figure 5:
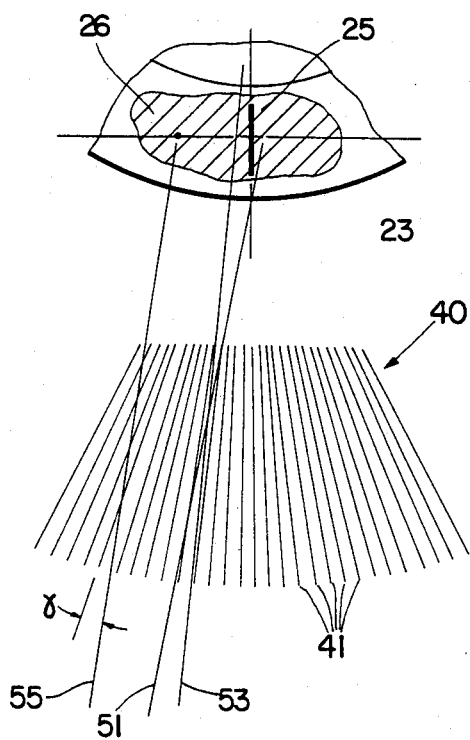
FIG. 5 is a diagrammatic illustration of the manner in which off-focal radiation is attenuated in accordance with the present invention.

FIG. 5 depicts the manner in which the secondary collimator 40 attenuates off-focal radiation. The degree to which on-focal ray paths 51, 53 are free to pass through the baffle openings is contrasted with the attenuation of an off-focal ray 55. As can be seen, the relative spacing between adjacent baffles as well as their distance from the focal spot bears on the amount of off-focal as well as on-focal radiation that is attenuated.

The degree to which an off-focal ray, such as that shown at 55, will be attenuated is represented by the equation:

$$\text{Attenuation} = e^{-\mu(nt/\cos\gamma)} \quad (1)$$

where
  $\mu$ is the attenuation coefficient of the baffle material at a given beam energy;
  t is the baffle thickness;
  n is the number of baffles an off-focal ray must pass through; and
  $\gamma$ is the angle between the off-focal ray path and the adjacent baffle.

It can readily be seen that the further from the focal spot an off-focal ray originates, the higher degree of attenuation it will experience.

Figure 6:
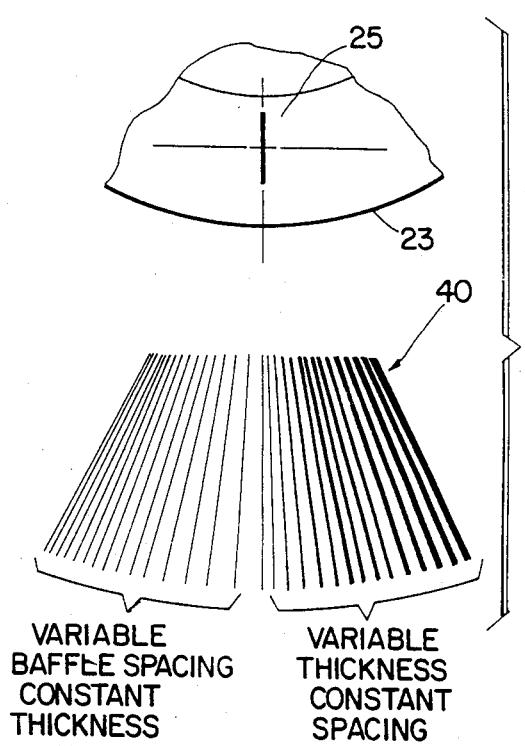
FIG. 6 is a diagrammatic representative of different embodiments of the beam compensator.

Referring now to FIG. 6, it can also be seen that by varying the spatial density of the baffles 41, the intensity of the unattenuated on-focal radiation passing through collimator 40 can be shaped to any desired profile. As discussed earlier, prior art beam compensators are disposed in the beam path and cause spectral changes in the beam through photoelectric absorption and also create unwanted scatter radiation. By varying the spatial density of the baffles, the collimator 40 acts as a beam compensator (as well as an off-focal collimator) without causing spectral changes to the emergent beam and without creating appreciable scatter.

The spatial density of the baffles can be varied in a number of ways, however only two will be discussed. First, baffles of constant thickness, t, are arranged such that the center-to-center spacing between adjacent baffles varies as a function of the degree of beam compensation desired. In the preferred embodiment, the spacing between adjacent baffles decreases as a function of distance from the center of the collimator housing 43. The emergent beam is thus shaped to have higher radiation intensity in its central portion with the intensity level decreasing as a function of distance from the central ray 57.

A second way to vary the spatial density is to vary the thickness of the baffles as a function of beam compensation while keeping the center-to-center spacing constant. In the preferred embodiment, the thickness of the baffles increases as a function of distance from the center of the collimator housing 43. This arrangement shapes the beam profile in the same manner as that described above.

In both of the above-described embodiments, the spatial density of the elements increases as the angle $\theta$ from the central ray 57 increases. In this manner, the radiation intensity across the beam profile corresponds to the generally elliptical shape of a cross-section of the human anatomy. However, it is recognized that the spatial density of the elements can be arranged in any number of ways in order to shape the beam profile to the attenuation characteristic of any shaped object under examination.

Figure 7:
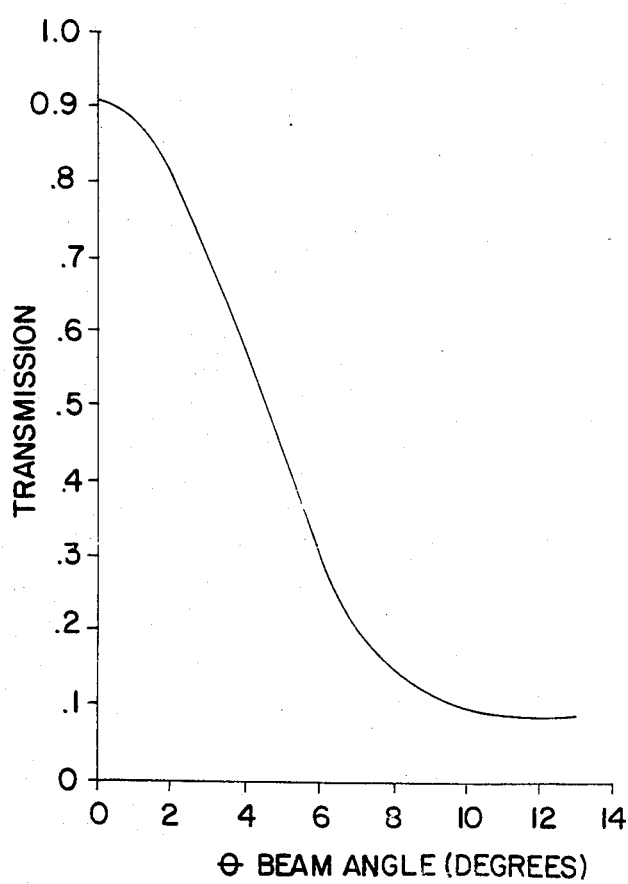
FIG. 7 is a graphical illustration of an exemplary beam compensation profile.

FIG. 7 shows an exemplary beam compensation curve. Transmission of the radiation beam through the compensator is plotted against $\theta$, the angle measured from the central ray 57 of the fan-shaped beam. In this example, as in the preferred embodiment of the invention, the density of the elements increases as the angle from the central ray 57 increases.

The invention has been described with reference to the preferred embodiment. Obviously, modifications and alterations will occur to others upon reading and understanding the preceding detailed description of the preferred embodiment. It is intended that the invention be construed as including all such alterations and modifications insofar as they come within the scope of the appended claims or the equivalents thereof.

Having thus described the preferred embodiment, the invention is now claimed to be:

1. An X-ray apparatus comprising:
  (a) an X-ray source having a focal spot from which said source propagates a beam of X-radiation along a beam path;
  (b) a primary collimator spaced from the source and mounted in the beam path for delineating the perimeter of said beam; and
  (c) a secondary collimator fixedly interposed between the source and the primary collimator for substantially blocking off-focus radiation while allowing substantially all on-focal radiation to pass, said secondary collimator including a plurality of thin radiation absorbing plates supported in spaced relationship with respect to one another in a housing such that each plate is aligned along a radii extending from said focal spot.

2. The X-ray apparatus of claim 1 wherein the spatial density of said radiation absorbing plates varies as a function of their location within said housing.

3. The X-ray apparatus of claim 1 wherein the length of said secondary collimator along said beam path is greater than its thickness.

4. An attenuator positioned proximate the focal spot of a radiation source for substantially blocking off-focal radiation while passing a substantially continuous beam of on-focal radiation without substantial modification of the beam spectrum, said attenuator comprising:
(a) a housing structure, and
(b) an array of thin radiation absorbing elements fixedly mounted within said housing in spaced relationship to one another such that the longitudinal dimension of said elements converge toward the focal spot of said radiation source.

5. The attenuator of claim 4 wherein the center-to-center spacing of said elements is constant and the thickness of said elements varies as a function of their location within the housing.

6. The attenuator of claim 5 wherein the thickness of the elements increases as a function of distance from the center of said housing.

7. The attenuator of claim 4 wherein the center-to-center spacing of said elements varies as a function of their location within the housing and the thickness of said elements is constant.

8. The attenuator of claim 7 wherein the center-to-center spacing between said elements decreases as a function of distance from the center of said housing.

9. In an X-ray apparatus having a source of X-radiation positioned to direct a beam of radiation emanating from a focal point along a path toward a subject under examination, the improvement of a dose compensator disposed along the beam path comprising:
(a) a collimator means mounted at a location spaced from the source for delineating the perimeter of the beam, and
(b) an attenuator means fixedly interposed between the collimator means and the source for providing a non-uniform beam intensity distribution without substantial modification of the beam spectrum comprising an array of radiation absorbing elements mounted in spaced relationship such that the spatial density of the elements varies as a function of intensity distribution.

10. The X-ray apparatus of claim 9 wherein the longitudinal dimension of said radiation absorbing elements are disposed radially relative to the focal point.

11. A computed tomography scanner comprising:
(a) a scan circle adapted to receive an object to be examined;
(b) a source of a substantially planar fanshaped beam of radiation, said source mountef for rotation about the scan circle;
(c) radiation detection means for detecting radiation emanating from said source and transversing the scan circle, said detector means at least partially encircling the scan circle; and
(d) an off-focal collimator for substantially attenuating off-focal radiation emanating from the source while passing a substantially continuous beam of on-focal radiation, said collimator means comprising an array of radiation absorbing elements fixedly mounted with respect to the source and disposed between the source and the scan circle, said elements defining an arc having its center substantially coincident with said source.

12. A computed tomography scanner comprising:
(a) a scan circle adapted to receive an object to be examined;
(b) a source of a substantially continuous fan-shaped beam of radiation, said source mounted for rotation about the scan circle;
(c) radiation detection means for detecting radiation emanating from said source and transversing the scan circle, said detector means at least partially encircling the scan circle; and
(d) a radiation compensator for varying the intensity of the radiation while maintaining substantial continuity of the fan beam comprising an array of radiation absorbing elements fixedly mounted with respect to the source and disposed between the source and the scan circle as a function of desired intensity variation.

13. An X-ray apparatus comprising:
(a) an X-ray tube housing defining a beam port through which radiation can pass;
(b) an X-ray tube havng a focal spot for generating a beam of penetrative radiation along a path originating from said focal spot, said tube mounted within the housing and aligned with the port such that the central axis of the beam substantially coincides with the central axis of the port;
(c) a primary collimator spaced from the tube housing and mounted in the beam path for delineating the perimeter of said beam;
(d) an off-focal radiation collimator fixedly mounted in the beam port between said tube and primary collimator for substantially absorbing off-focal radiation emanating from said tube, said off-focal radiation collimator comprising:
(i) a collimator housing, and
(ii) a plurality of radiation absorbing baffles within the collimator housing, said baffles radially disposed relative to the focal spot.

14. A method for shaping the profile of a continuous beam of radiation without creating substantial discontinuities in the shape beam utilizing a source of radiation for propagating said continuous beam of radiation along a path, said method comprising the steps of:
(a) radially aligning thin radiation absorbing elements in fixed relation to the source;
(b) interposing said elements in the beam path; and
(c) varying the spatial density of said elements as a function of the desired beam profile.

15. An X-ray apparatus comprising:
(a) an X-ray source having an anode from which X-rays originate when bombarded with electrons, said anode having a first area from which rays of on-focal radiation originate and a second area extending beyond said first area from which rays of off-focal radiation originate; and
(b) an off-focal collimator fixedly mounted in spaced relationship from said source for passing substantially all on-focal radiation rays and for attenuating off-focal radiation rays wherein off-focal rays experience greater attenuation the further from said first area said off-focal rays originate.

16. In an X-ray apparatus having a source of X-radiation positioned to direct a beam of radiation emanating from a focal point along a path toward a subject under examination, the improvement of a dose compensator fixedly disposed along the beam path comprising an array of thin radiation absorbing elements mounted in spaced relationship with the longitudinal dimension of the elements focussed on the source such that the spatial density of the elements varies as a function of the attenuation characteristics of the object under examination without substantially modifying the energy spectrum of the beam.

17. A computed tomography scanner comprising:
  (a) a scan circle adapted to receive an object to be examined;
  (b) a source of radiation mounted for rotation about the scan circle, said source including;
    (i) a housing defining a beam port, and
    (ii) an X-ray tube mounted in said housing having a focal spot for generating a beam of penetrative radiation along a path originating from said focal spot and passing through said beam port;
  (c) radiation detection means for detecting radiation enamating from said source and transversing said scan circle, said detector means at least partially encircling the scan circle;
  (d) attenuator means fixedly mounted in said beam port, said attenuator means comprising;
    (i) an array of radiation absorbing elements mounted in spaced relationship and radially disposed relative the focal spot for attenuating substantially all off-focal radiation emanating from said source, and
    (ii) wherein the spatial density of said elements varies for shaping the intensity profile of said beam.

18. The computed tomography scanner of claim 17 wherein the center to center spacing of said attenuator elements is constant and the thickness of said elements varies as a function of desired intensity profile.

19. The computed tomography scanner of claim 18 wherein the thickness of the elements increases as a function of distance from the center of said array.

20. The computed tomography scanner of claim 17 wherein the center to center spacing of said elements varies as a function of desired intensity profile and the thickness of said elements is constant.

21. The computed tomography scanner of claim 20 wherein the center to center spacing between said elements decreases as a function of distance from the center of said array.

22. A Computed Tomography Scanner comprising:
  (a) a scan circle adapted to receive an object to be examined;
  (b) a source of a substantially continuous fan-shaped beam of radiation mounted for rotation about the scan circle;
  (c) an array of closely spaced radiation detectors for detecting radiation from said source and transversing said scan circle, said detector array at least partially encircling the scan circle; and
  (d) an off-focal collimator means fixedly mounted with respect to said source and interposed in the radiation beam for blocking off-focal radiation emanating from the source without introducing substantial discontinuities in the fan-shaped beam, said off-focal collimator comprising a plurality of thin, radiation absorbing elements fixedly mounted in spaced relationship to one another such that each element is aligned along radii extending from said source.

23. A method for shaping the profile of a beam of radiation while simultaneously eliminating off-focal radiation present in the beam without creating substantial discontinuities in the shaped beam or substantially modifying the energy spectrum of the beam, said method comprising the steps of:
  (a) directing a beam of radiation originating from a source along a path;
  (b) radially aligning thin, radiation absorbing elements relative to the source;
  (c) varying the spatial density of said elements as a function of the desired beam profile;
  (d) interposing said elements in the beam path; and
  (e) fixing said elements in relation to said source.

24. Apparatus for attenuating off-focal radiation emanating from a radiation souce while simultaneously shaping the intensity profile of on-focal radiation, said apparatus comprising an array of thin, finely spaced radiation absorbing elements radially aligned in fixed relationship with said source, wherein the spatial density of said elements varies as a function of desired intensity profile.

* * * * *